(12) United States Patent
Samady et al.

(10) Patent No.: US 11,341,645 B2
(45) Date of Patent: May 24, 2022

(54) METHODS AND SYSTEMS FOR DETERMINING CORONARY HEMODYNAMIC CHARACTERISTIC(S) THAT IS PREDICTIVE OF MYOCARDIAL INFARCTION

(71) Applicant: Emory University, Atlanta, GA (US)

(72) Inventors: Habib Samady, Atlanta, GA (US); Alessandro Veneziani, Decatur, GA (US); Don Giddens, Hilton Head Island, SC (US); David Molony, Atlanta, GA (US); Adrien Lefieux, Decatur, GA (US); Arnav Kumar, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/978,489

(22) PCT Filed: Mar. 11, 2019

(86) PCT No.: PCT/US2019/021646
§ 371 (c)(1),
(2) Date: Sep. 4, 2020

(87) PCT Pub. No.: WO2019/173830
PCT Pub. Date: Sep. 12, 2019

(65) Prior Publication Data
US 2021/0056697 A1 Feb. 25, 2021

Related U.S. Application Data

(60) Provisional application No. 62/640,939, filed on Mar. 9, 2018.

(51) Int. Cl.
*G06K 9/00* (2022.01)
*G06T 7/00* (2017.01)
(Continued)

(52) U.S. Cl.
CPC .............. *G06T 7/0014* (2013.01); *G06T 7/11* (2017.01); *G16H 30/40* (2018.01); *G16H 50/30* (2018.01);
(Continued)

(58) Field of Classification Search
CPC .................... G06T 7/0014; G06T 7/11; G06T 2207/30048; G06T 2207/30096;
(Continued)

(56) References Cited

U.S. PATENT DOCUMENTS 10,092,247 B2 * 10/2018 Taylor .................. A61B 5/021
2008/0228086 A1 9/2008 Ilegbusi et al.
(Continued)

FOREIGN PATENT DOCUMENTS

WO WO2013071219 A1 5/2013

OTHER PUBLICATIONS

Han et al. "Relationship Between Endothelial Wall Shear Stress and High-Risk Atherosclerotic Plaque Characteristics for Identification of Coronary Lesions That Cause Ischemia: A Direct Comparison With Fractional Flow Reserve." Journal of the American Heart Association, 2016; 5:e004186.
(Continued)

*Primary Examiner* — Atiba O Fitzpatrick
(74) *Attorney, Agent, or Firm* — Emory Patent Group (57) ABSTRACT

The systems and methods can accurately and efficiently determine a myocardial risk from a lesion disposed along a coronary segment using hemodynamic characteristic(s) associated with one or more sections of the corresponding lesion site. The method may include segmenting one or more lesion sites disposed along at least one arterial segment of the one or more arterial segments of the coronary model into one or more sections. Each lesion site includes a lesion. The method may include determining one or more characteristics
(Continued)

for at least one section using at least the one or more characteristics associated with the at least one arterial segment. The one or more characteristics for the at least one section including hemodynamic force characteristic(s) (e.g., wall shear stress (WSS)). The method may include determining one or more risk indices for each lesion site using at least the hemodynamic force characteristic(s) for the at least one section.

16 Claims, 5 Drawing Sheets (51) Int. Cl.
*G06T 7/11* (2017.01)
*G16H 50/30* (2018.01)
*G16H 30/40* (2018.01)
*A61B 5/00* (2006.01)
*A61B 5/026* (2006.01)
*A61B 6/00* (2006.01)
*A61B 8/06* (2006.01)
*A61B 8/12* (2006.01)

(52) U.S. Cl.
CPC ........... *A61B 5/0066* (2013.01); *A61B 5/0263* (2013.01); *A61B 6/507* (2013.01); *A61B 8/065* (2013.01); *A61B 8/12* (2013.01); *G06T 2207/30048* (2013.01); *G06T 2207/30096* (2013.01); *G06T 2207/30104* (2013.01)

(58) Field of Classification Search
CPC ......... G06T 2207/30104; G06T 7/0012; G06T 7/10; G06T 2207/30101; G16H 50/30; G16H 30/40; A61B 5/0066; A61B 5/0263; A61B 6/507; A61B 8/065; A61B 8/12

See application file for complete search history.

(56) References Cited

U.S. PATENT DOCUMENTS

| 2010/0249620 | A1  | 9/2010  | Cho         |              |
|--------------|-----|---------|-------------|--------------|
| 2011/0173027 | A1* | 7/2011  | Olszewski   | G16H 20/10   |
|              |     |         |             | 705/2        |
| 2012/0041320 | A1* | 2/2012  | Taylor      | A61B 5/1075  |
|              |     |         |             | 600/508      |
| 2015/0065846 | A1* | 3/2015  | Choi        | A61B 5/02007 |
|              |     |         |             | 600/407      |
| 2015/0164342 | A1* | 6/2015  | Choi        | A61B 5/02007 |
|              |     |         |             | 600/407      |
| 2017/0014033 | A1* | 1/2017  | Koo         | G16H 50/30   |
| 2018/0243033 | A1  | 8/2018  | Tran et al. |              |
| 2018/0336319 | A1* | 11/2018 | Itu         | G16H 50/70   |
| 2021/0244475 | A1* | 8/2021  | Taylor      | A61B 5/024   |

OTHER PUBLICATIONS

Corban et al. "Wall shear stress and evolution of coronary atherosclerosis: An emerging intravascular imaging modality." Interventional Cardiology, 2012; 4:155-157.
International Search Report for PCT Application No. PCT/US2019/021646 dated May 30, 2019.
International Preliminary Report on Patentability for PCT Application No. PCT/US2019/021646 dated Sep. 15, 2020.

* cited by examiner

METHODS AND SYSTEMS FOR DETERMINING CORONARY HEMODYNAMIC CHARACTERISTIC(S) THAT IS PREDICTIVE OF MYOCARDIAL INFARCTION

CROSS-REFERENCE TO RELATED APPLICATIONS

This application is the National Stage of International Application No. PCT/US2019/021646 filed Mar. 11, 2019, which claims the benefit of U.S. Provisional Application No. 62/640,939 filed Mar. 9, 2018. The entirety of each of these applications is hereby incorporated by reference for all purposes.

BACKGROUND

Coronary heart disease (CHD) is the most common cause of death in the U.S. CHD results from atherosclerosis that can progress and lead to ischemia and angina. Fractional flow reserve (FFR) recently has become an invasive physiologic index of epicardial lesion severity. FFR generally has been used to guide treatment decisions, for example, whether to treat the patient with medical therapy and/or revascularization (e.g., stent placement or coronary artery bypass graft (CABG) surgery, to improve flow across obstructive lesions). However, it has been found that patients having coronary lesions with low fractional flow reserve (FFR) treated with medical therapy alone can have higher rates of subsequent major adverse myocardial infarctions (MACE), a composite of death, myocardial infarction, and urgent revascularization. Additionally, no currently existing hemodynamic index methods have been shown to be associated with myocardial infarction. Therefore, current methods to evaluate lesions and risks associated thereof may not be as effective, and therefore can negatively affect the quality of care, the patient experience, and the cost of health care delivery.

SUMMARY

Thus, there is a need for systems, softwares and methods that can identify coronary lesion(s) that is predictive of myocardial infarction, as these regions could be preemptively treated percutaneously or systemically. This can provide clinicians with a more effective tool in clinical medical decision-making.

In some embodiments, the methods may include a computer-implemented method of determining a risk of myocardial infarction associated with a coronary lesion of a patient. In some embodiments, the method may include receiving a patient-specific coronary model of at least a portion of a vasculature of the patient. The patient-specific coronary model may include a geometrical representation of the one or more arterial segments. The patient-specific coronary model may include one or more characteristics associated with each arterial segment. In some embodiments, the method may include segmenting each lesion site disposed along at least one arterial segment of the one or more arterial segments into one or more sections. Each lesion site may include a lesion. The method may also include determining one or more characteristics for at least one section of the one or more sections of each lesion site using at least the one or more characteristics associated with the at least one arterial segment. The one or more characteristics for the at least one section may include one or more force hemodynamic characteristics. The one or more hemodynamic force characteristics for the at least one section may include at least wall shear stress (WSS). In some embodiments, the method may include determining one or more risk indices for each lesion site using at least the one or more hemodynamic force characteristics for the at least one section of each lesion site. The one or more risk indices for each lesion site may indicate or represent a risk or probability of a myocardial infarction event from each lesion site.

In some embodiments, the determining the one or more force hemodynamic characteristics for the at least one section of each lesion site may include averaging the one or more force hemodynamic characteristics along the at least one section of the lesion site using the one or more force hemodynamic characteristics for the at least one arterial segment.

In some embodiments, the segmenting of each lesion site into one or more sections may be based on a location of the lesion of each lesion site relative to corresponding arterial segment. In some embodiments, each lesion site may be segmented into at least three sections.

In some embodiments, the one or more sections for each lesion site may include a proximal section, the proximal section being adjacent to inflow boundary of the corresponding arterial segment. The one or more hemodynamic force characteristics may be determined for at least the proximal section of each lesion site. The one or more risk indices for each lesion site may be determined using the one or more hemodynamic force characteristics determined for at least the proximal section.

In some embodiments, the method may further include identifying one or more lesion sites disposed along the at least one arterial segment of the one or more arterial segments. Each lesion site may include the lesion. The one or more characteristics associated with each arterial segment and each lesion site may include one or more hemodynamic characteristics. The one or more hemodynamic characteristics may include one or more pressure characteristics. The one or more pressure characteristics may include at least fractional flow reserve (FFR). The one or more lesion sites may be identified and/or the one or more risk indices may be determined using at least the one or more pressure characteristics for the one or more sections of each lesion site and/or for each arterial segment.

In some embodiments, the determining the one or more risk indices may include comparing at least the one or more hemodynamic force characteristics for the at least one section of each lesion site to one or more thresholds.

In some embodiments, the method may further include generating a visualization of at least one lesion site. The method may include outputting the visualization.

In some embodiments, the visualization may include (i) the one or more risk indices associated with the at least one lesion site and/or (ii) the one or more characteristics associated with the at least one lesion site and/or the one or more arterial segments.

In some embodiments, the method may further include enabling an assessment of treatment options for each lesion site, based on the one or more risk indices and/or the one or more characteristics associated with the one or more sections of each lesion site.

In some embodiments, the method may further include receiving patient data of the patient, the patient data may include medical image data of the patient acquired by a medical image acquisition device. The medical image data may include the one or more arterial segments and surrounding area. The method may further include generating the patient-specific coronary model using the patient data. The coronary model may include the geometrical representation of the one or more arterial segments from the medical image data, boundaries for each arterial segment, boundary conditions for each arterial segment, geometrical information for each boundary, and geometrical information. In some embodiments, the generating may include generating the one or more characteristics for each arterial segment. The one or more characteristics for each arterial segment may include one or more flow field characteristics and one or more hemodynamic characteristics.

In some embodiments, the systems may include a system for determining a risk of myocardial infarction associated with a coronary lesion site of a patient. The system may include at least one processor; and a memory. In some embodiments, the processor may be configured to cause receiving a patient-specific coronary model of at least a portion of a vasculature of the patient. The patient-specific coronary model may include a geometrical representation of the one or more arterial segments. The patient-specific coronary model may include one or more characteristics associated with each arterial segment. The processor may be configured to cause segmenting each lesion site disposed along at least one arterial segment of the one or more arterial segments into one or more sections. Each lesion site may include a lesion. The processor may be configured to cause determining one or more characteristics for at least one section of the one or more sections of each lesion site using at least the one or more characteristics associated with the at least one arterial segment. The one or more characteristics for the at least one section may include one or more force hemodynamic characteristics. The one or more hemodynamic force characteristics for the at least one section may include at least wall shear stress (WSS).

In some embodiments, the processor may be configured to cause determining one or more risk indices for each lesion site using at least the one or more hemodynamic force characteristics for the at least one section of each lesion site. The one or more risk indices for each lesion site may indicate a risk of a myocardial infarction event due to each lesion site.

In some embodiments, the determining the one or more force hemodynamic characteristics for the at least one section of each lesion site may include averaging the one or more force hemodynamic characteristics along the at least one section of the lesion site using the one or more force hemodynamic characteristics for the at least one arterial segment.

In some embodiments, the segmenting of each lesion site into one or more sections may be based on a location of the lesion of each lesion site relative to corresponding arterial segment. In some embodiments, each lesion site may be segmented into at least three sections.

In some embodiments, the one or more sections for each lesion site may include a proximal section, the proximal section being adjacent to inflow boundary of the corresponding arterial segment. The one or more hemodynamic force characteristics may be determined for at least the proximal section of each lesion site. The one or more risk indices for each lesion site may be determined using the one or more hemodynamic force characteristics determined for at least the proximal section.

In some embodiments, the processor may be further configured to cause identifying one or more lesion sites disposed along the at least one arterial segment of the one or more arterial segments. Each lesion site may include the lesion. The one or more characteristics associated with each arterial segment and each lesion site may include one or more hemodynamic characteristic. The one or more hemodynamic characteristics associated may include one or more pressure characteristics. The one or more pressure characteristics may include at least fractional flow reserve (FFR). The one or more lesion sites may be identified and/or the one or more risk indices may be determined using at least the one or more pressure characteristics for the one or more sections of each lesion site and/or for each arterial segment.

In some embodiments, the determining the one or more risk indices may include comparing at least the one or more hemodynamic force characteristics for the at least one section of each lesion site to one or more thresholds.

In some embodiments, the processor may be further configured to cause generating a visualization of at least one lesion site. The processor may be further configured to cause outputting the visualization.

In some embodiments, the visualization may include (i) the one or more risk indices associated with the at least one lesion site and/or (ii) the one or more characteristics associated with the at least one lesion site and/or the one or more arterial segments.

In some embodiments, the processor may be further configured to cause enabling an assessment of treatment options for each lesion site, based on the one or more risk indices and/or the one or more characteristics associated with the one or more sections of each lesion site.

In some embodiments, the processor may be further configured to cause receiving patient data of the patient, the patient data may include medical image data of the patient acquired by a medical image acquisition device. The medical image data may include the one or more arterial segments and surrounding area. The processor may be further configured to cause generating the patient-specific coronary model using the patient data. The coronary model may include the geometrical representation of the one or more arterial segments from the medical image data, boundaries for each arterial segment, boundary conditions for each arterial segment, geometrical information for each boundary, and geometrical information. In some embodiments, the generating may include generating the one or more characteristics for each arterial segment. The one or more characteristics for each arterial segment may include one or more flow field characteristics and one or more hemodynamic characteristics.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems and methods of the disclosure can accurately and efficiently determine a risk of a cardiovascular event, such as a risk of myocardial infarction, associated with one or more lesion sites of a patient. The systems and methods can provide a near real-time (e.g., relatively short-time) evaluation of the myocardial infarction risk associated with one or more lesion sites of a patient, as well as treatment options, enabling a clinician to make a better determination of medical treatment, thereby improving the quality of healthcare for a patient.

In some embodiments, the risk can be indicative of the need for revascularization due to the risk of myocardial infarction from or due to that lesion site. Using the risk determined according to the disclosure, the disclosure can also provide a more accurate assessment of treatment options for the one or more lesion sites of patients, including those having stable coronary artery disease (CAD). The risk determined according to the disclosure can better stratify patients with stable CAD, including those who have lesion(s) with a positive FFR (e.g., an FFR value below a threshold (e.g., 0.8)), resulting in a more accurate identification of those patients who would benefit from revascularization (e.g., percutaneous coronary intervention (PCI), coronary artery bypass graft (CABG), other coronary interventions etc.)) over medical (e.g., pharmaceutical) therapy alone. Thus, the systems and methods can result in better outcomes for the patient (e.g., avoiding an urgent revascularization, etc.).

Figure 1:
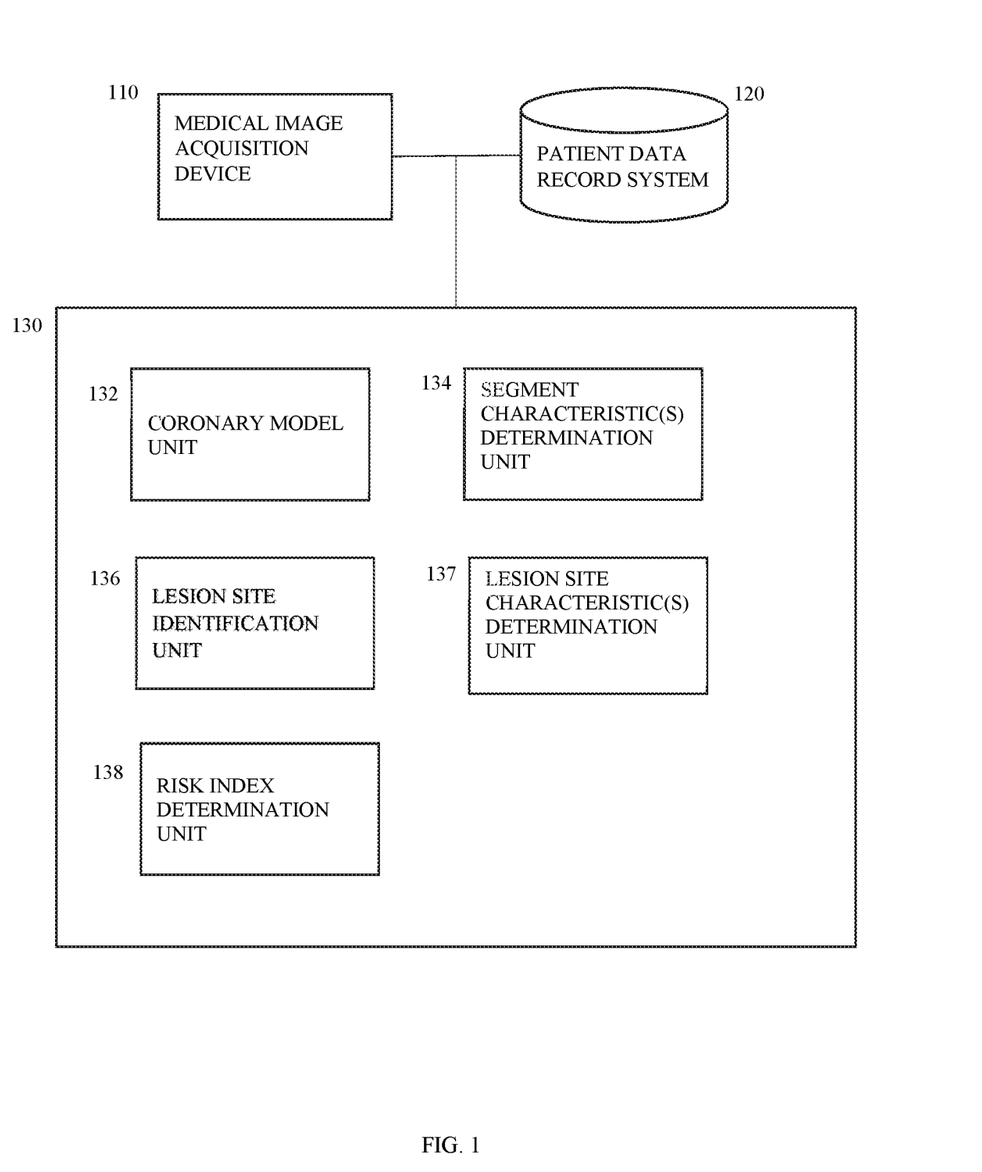
FIG. 1 shows an example of a system that can be used to determine risk index indicative of myocardial infarction according to some embodiments.

FIG. 1 shows a system 100 that can determine one or more risk indices associated with a lesion site indicative of a probability of a myocardial infarction due to the lesion site using at least one or more hemodynamic force characteristics associated with one or more sections of the lesion site.

In some embodiments, the system 100 may include a risk index determination device 130 configured to one or more risk indices associated with a lesion site indicative of a probability of a myocardial infarction due to the lesion site using at least one or more hemodynamic force characteristics associated with one or more sections of the lesion site. In some embodiments, the system 100 may optionally also include a medical image acquisition device 110 and/or a patient data database 120.

The one or more medical image acquisition devices 110 may be configured to acquire one or more medical images of a vascular system of a patient. In some embodiments, the medical image acquisition device 110 may include but is not limited to computed tomography (CT) scanner, intravascular ultrasound (IVUS) device, biplane angiography scanner, intravascular ultrasound (IVUS) device, optical coherence tomography (OCT) scanner, magnetic resonance imaging (MM) scanner, among others, or any combination thereof. The medical image data from one or more medical image acquisition devices may include but are not limited to CT, Dyna CT, magnetic resonance (MR), angiographic, ultrasound, OCT, single photon emission computed tomography (SPECT), among others, or any combination thereof. The medical image data can be 2D, 3D, or 4D (3D+time) medical image data. In some embodiments, the medical image data may be received directly from the one or more medical image acquisition devices 110, from a computer readable storage system (e.g., a patient data record system 120), among others, or any combination thereof.

In some embodiments, the system 100 may include a patient data record system 120 configured to store patient data, including physiological (such as blood or cuff pressure, baseline heart rate, height, weight, hematocrit, stroke volume, etc.), demographic, medical image data, blood markers data, among other types of data, among others, or any combination thereof. For example, the patient data database may be an electronic health record system. The patient data record system 120 may include one or more medical image storage devices configured to store the medical images acquired by the medical image acquisition device 110. In some embodiments, the patient data record system 120 may also be configured to store generated coronary models and associated metrics, values, etc.

In some embodiments, the risk index determination device 130 may include a coronary model unit 132 (i) configured to construct a coronary model using at least the acquired medical image data and related information (e.g., boundaries, geometrical or anatomical information, characteristics, among others, or any combination thereof) and/or (ii) configured to retrieve or receive a generated coronary model and related information (e.g., boundaries, geometrical or anatomical information, characteristics, among others, or any combination thereof) from memory from another device, such as the patient data record system 120.

For example, the coronary model may be based on medical image data, such as angiographic data, CT image data, or MR data. In some embodiments, the coronary model may also be constructed using patient physiological data. The coronary model may include a geometrical representation of one or more arterial segments from at least the acquired medical image data, boundaries associated with the geometrical representation, geometrical information associated with each boundary, among others, or any combination thereof. In some embodiments, the geometrical representation may be a multi-dimensional (3-D or 4-D) digital model of the spatial volume of one or more arterial segments.

In some embodiments, the coronary model may include boundary conditions associated with the geometrical representation. In some embodiments, the coronary model, the boundary conditions, and/or values of one or more characteristics and/or information may be generated, calculated, measured, and/or obtained using any available methods including various invasive methods, non-invasive methods, or combination of methods, such as methods using empirical laws, physiology-derived features, physics-derived features, allometric scaling laws (e.g., Murray's law), Navier-Stokes equations, data assimilation, machine learning, among others, or any combination thereof.

The one or more arterial segments may include a portion of one or more arteries and one or more branches that extend therefrom. In some embodiments, the one or more arterial segments may include one or more coronary arterial segments. The one or more coronary arterial segments may include a portion of one or more coronary arteries emanating from an aorta of a subject and one or more branches that extend therefrom.

In some embodiments, if the coronary model unit 132 receives image data to generate a coronary model, the coronary model unit 132 may be configured to determine boundaries for each arterial segment using any available methods. "Boundaries" may refer to cross-sections of the representation of the arterial segment and may include but are not limited to: inflow boundary corresponding to the cross-section through which the blood flows; one or more outflow boundaries corresponding to the cross-section disposed downstream or distal from the inflow boundary through which blood flow is directed outward; one or more vessel wall boundaries corresponding to an interface between the inner surface of the arterial wall and the flowing blood; among others; or combination thereof.

In some embodiments, for the generation of the coronary model, the coronary model unit 132 may be configured to determine geometrical information for each boundary for each segment using the generated geometric representation. In some embodiments, the geometrical information may include but is not limited to radius, diameter, circumference, area, among others, or any combination thereof.

In some embodiments, for the generation of the coronary model, the coronary model unit 132 may be configured to determine boundary conditions for each boundary for each arterial segment, use stored boundary conditions for each boundary for each arterial segment, or any combination thereof. By way of example, the boundary conditions for each segment may include inflow boundary condition, outflow boundary conditions, one or more vessel wall boundary conditions, among others, or any combination thereof. The inflow boundary condition may be a value or a range of values for velocity, flow rate, pressure or other characteristics. Each outflow boundary condition may be a value or a range of values for velocity, flow rate, pressure, a percentage of inflow boundary, or other characteristic. Each vessel wall boundary condition may be a value or a range of values for velocity, flow rate, pressure, any combination thereof, or other characteristic.

In some embodiments, the device 130 may include a segment characteristics determination unit 134 (i) configured to determine one or more characteristics associated with each arterial segment using any of the available methods, and/or (ii) configured to retrieve or receive the one or more characteristics from another device, such as the patient data record system 120. For example, the one or more characteristics may be stored with the corresponding generated coronary model and related information (e.g., boundary condition, geometrical information, etc.) in the patient data record system 120 and/or other storage medium. In some embodiments, the segment characteristic(s) determination unit 134 may be a part of the coronary model unit 132, for example, so that the one or more characteristics are determined with the generated coronary model.

In some embodiments, the one or more characteristics associated with each arterial segment may include one or flow field characteristics, one or more hemodynamic characteristics (which can be referred to as "one or more segment hemodynamic characteristics"), among others, or any combination thereof.

In some embodiments, the flow field characteristics may include but is not limited to pressure field, velocity field, among others, or any combination thereof.

In some embodiments, the one or more hemodynamic characteristics may include but is not limited to one or more pressure characteristics, one or more hemodynamic force characteristics, among others, or any combination thereof. For example, the one or more pressure characteristics may include fractional flow reserve (FFR), instantaneous wave-free ratio (iFR), absolute flow reserve (aFR), relative flow reserve (RFR), diastolic pressure ratio (dPR), other pressure characteristic(s) (e.g., pressure across the segment, pressure difference across the segment, etc.), among others, or any combination thereof. In some embodiments, the one or more hemodynamic force characteristics (also referred to as "hemodynamic endothelial force characteristics") may include but is not limited to wall shear stress (WSS), axial plaque stress (APS), among others, or any combination thereof.

In some embodiments, the one or more characteristics associated with the coronary model may be determined using any available methods including various invasive methods, non-invasive methods, or combination of methods, such as methods using empirical laws, physiology-derived features, physics-derived features, allometric scaling laws (e.g., Murray's law), Navier-Stokes equations, data assimilation, machine learning, among others, or any combination thereof.

In some embodiments, the device 130 may include a lesion site identification unit 136 that (i) can be configured to determine one or more lesion sites disposed along one or more arterial segments of the coronary model and/or (ii) configured to retrieve or receive the location and/or information associated with one or more lesion sites from another device, such as the patient data record system 120. For example, the one or more lesion sites may be stored with the corresponding generated coronary model, e.g., in the patient data record system 120.

In some embodiments, each lesion site may include a lesion, a stenosis, and/or plaque. In some embodiments, the one or more lesion sites may include one or more of a point, area, volume, cross-section, portion, and/or region within the one or more arterial segments of the coronary model. In some embodiments, each lesion site may also include a region of the arterial segment before and/or after each lesion.

In some embodiments, the lesion site identification unit 136 may be configured to determine and/or retrieve one or more lesion characteristics associated with each lesion. For example, the one or more lesion characteristics may include but is not limited to volume of plaque material, size, shape, one or more material properties, one or more mechanical properties, among others, or any combination thereof.

In some embodiments, the lesion site identification unit 136 may be configured to identify one or more lesion sites disposed along an arterial segment using the geometrical information, one or more characteristics associated with the arterial segment, one or more lesion characteristics, among others, or any combination thereof, according to available methods including machine learning.

In some embodiments, the lesion site identification unit 136 may optionally determine a stenosis index of functional severity for each lesion site using the geometrical information, the one or more characteristics, the one or more lesion characteristics, among others, or any combination thereof. In some embodiments, the lesion site identification unit 136 may use the stenosis index to identify which lesion sites to be further analyzed. For example, if the stenosis index is based on the FFR value for the segment, a lesion site may be identified for further analysis if the FFR value is equal to and/or below a threshold (e.g., 0.8).

In some embodiments, the location of the lesion site(s) and associated information (e.g., the one or more lesion characteristics, stenosis index, etc.) among others, may be stored with the corresponding generated coronary model, for example, in the patient data record system 120.

In some embodiments, the lesion site identification unit 136 may be configured to segment the one or more identified lesion sites (e.g., identified and/or retrieved by the lesion identification unit 136) into one or more sections. In some embodiments, the one or more sections of each lesion site may include one or more sections of the lesion. By way of example, the one or more sections of each lesion site may include a proximal section of the lesion (next to the upstream section), a middle section of the lesion (between the proximal and distal section), a distal section of the lesion. In some embodiments, the one or more sections may include the regions before (upstream) and after (downstream) of the lesion. The sections of each lesion site may be relative to the location of the lesion site with respect to the associated arterial segment. In some embodiments, the lesion site identification unit 136 may include less, more, and/or different sections.

In some embodiments, the device 130 may include a lesion site characteristic(s) determination unit 137 that can be configured to determine one or more characteristics associated with each lesion site (which can be referred to as "one or more lesion site hemodynamic characteristics"), for example, using the one or more hemodynamic characteristics determined for the corresponding arterial segment.

In some embodiments, the lesion site characteristic(s) determination unit 137 may be configured to determine one or more characteristics for one or more sections of each lesion site using the one or more characteristics determined for the corresponding arterial segment. The one or more characteristics determined for one or more sections of the lesion site may include at least one or more hemodynamic force characteristics. The one or more hemodynamic force characteristics (also referred to "hemodynamic endothelial force characteristics") may include but is not limited to wall shear stress (WSS), axial plaque stress (APS), among others, or any combination thereof. In some embodiments, the one or more hemodynamic force characteristics may include at least the WSS.

In some embodiments, the lesion site characteristic(s) determination unit 137 may determine additional characteristic(s) for the one or more sections of each lesion site. For example, the lesion site characteristic(s) determination unit 137 may determine at least another characteristic of the one or more hemodynamic characteristics, such as one or more pressure characteristics. The one or more pressure characteristics may include but is not limited to fractional flow reserve (FFR), instantaneous wave-free ratio (iFR), absolute flow reserve (aFR), relative flow reserve (RFR), diastolic pressure ratio (dPR), other pressure characteristics (e.g., pressure across the segment, pressure difference across the segment, etc.), among others, or any combination thereof. In some embodiments, the other characteristic(s) may at least include FFR for the one or more sections.

In some embodiments, the device 130 may include a risk index determination unit 138 that may be configured to determine one or more risk indices associated with each lesion site using at least the one or more hemodynamic force characteristics. The one or more risk indices may be indicative of a probability of a myocardial infarction event due to the lesion site. In some embodiments, the one or more risk indices for each lesion site may be based on at least one or more hemodynamic force characteristics associated with one or more sections of that lesion site.

By way of example, the risk index determination unit 138 may be configured to determine the one or more risk indices associated with a lesion site using at least the WSS value determined for one or more sections of the lesion site. In some embodiments, the one or more risk indices for a lesion site may also be based on at least another characteristic of the one or more characteristics determined for one or more sections of the lesion site (e.g., one or more pressure characteristics (e.g., FFR)), stenosis index, one or more lesion characteristics, among others, or any combination thereof.

The device 130 may interface with a user interface on which the coronary model may be displayed so that the user may select the coronary segment and/or lesion site at which the one or more risk indices can be determined; modify the coronary model and/or one or more risk indices for example, by treating the localized stenosis. In some embodiments, the device 130 may be configured to generate a visualization. The visualization may be capable of virtual intervention simulations using the coronary model, the one or more hemodynamic characteristics, the one or more lesion sites, and one or more risk indices. This way, clinicians can have the capability of making more personalized medical decisions for the patient.

In some embodiments, the medical image acquisition device 110, the patient data database 120 and the device 130, may have connectivity via a communication network. By way of example, the communication network of system 100 can include one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, NFC/RFID, RF memory tags, touch-distance radios, or any combination thereof. In addition, the wireless network may be, for example, a cellular network and may employ various technologies including enhanced data rates for global evolution (EDGE), general packet radio service (GPRS), global system for mobile communications (GSM), Internet Protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Although the systems/devices of the system 100 are shown as being directly connected, the systems/devices may be indirectly connected to one or more of the other systems/devices of the system 100. In some embodiments, a system/device may be only directly connected to one or more of the other systems/devices of the system 100.

It is also to be understood that the system 100 may omit any of the devices illustrated and/or may include additional systems and/or devices not shown. It is also to be understood that more than one device and/or system may be part of the system 100 although one of each device and/or system is illustrated in the system 100. It is further to be understood that each of the plurality of devices and/or systems may be different or may be the same. For example, one or more of the devices may be hosted at any of the other devices.

Figure 5:
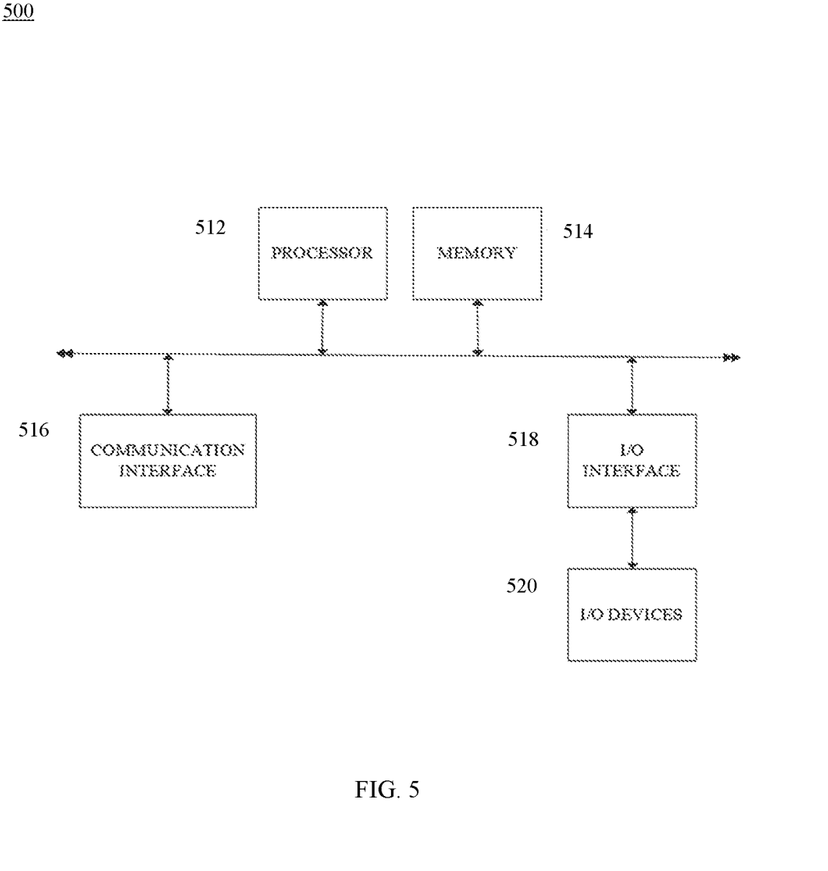
FIG. 5 shows a block diagram illustrating an example of a computing system.

In some embodiments, any of the devices of the system 100 may include a non-transitory computer-readable medium storing program instructions thereon that is operable on a user device. A user device may be any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, or any combination thereof, including the accessories and peripherals of these devices, or any combination thereof. FIG. 5 shows an example of a user device.

Figure 2:
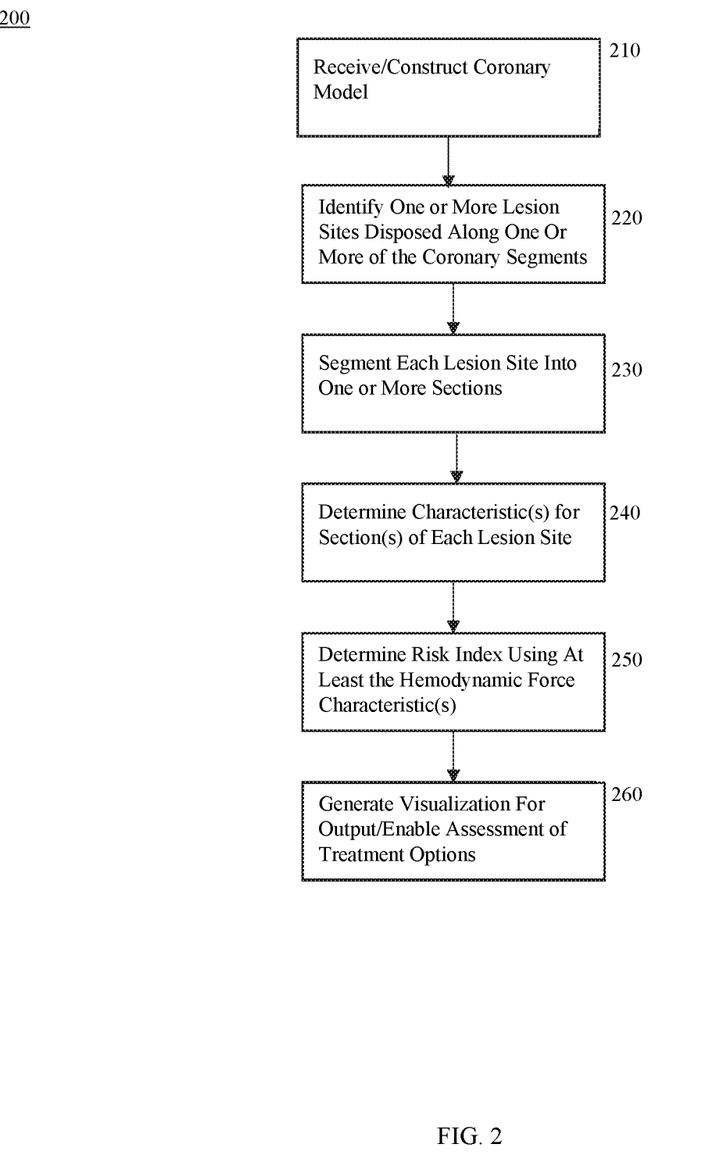
FIG. 2 shows a method of determining risk of myocardial infarction according to some embodiments.

FIG. 2 shows a method of determining one or more risk indices associated with a lesion site indicative of a probability of a myocardial infarction event due to the lesion site using at least one or more hemodynamic force characteristics associated with one or more sections of the lesion site. Unless stated otherwise as apparent from the following discussion, it will be appreciated that terms such as "updating," "modifying," "constructing," "generating," "determining," "displaying," "obtaining," "processing," "computing," "selecting," "receiving," "detecting," "estimating," "calculating," "quantifying," "outputting," "acquiring," "analyzing," "enabling," "retrieving," "inputting," "assessing," "performing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. The system for carrying out the embodiments of the methods disclosed herein is not limited to the systems shown in FIGS. 1 and 5. Other systems may also be used.

The method of the disclosure is not limited to the steps described herein. The steps may be individually modified (e.g., including adding additional steps) and/or omitted. It will be also understood that at least some of the steps may be performed in parallel.

In some embodiments, the method 200 may include a step 210 of receiving a coronary model for the patient. The coronary model may include a geometrical representation of one or more arterial segments from at least acquired medical image data. In some embodiments, the geometrical representation may be a multi-dimensional (e.g., 3-D or 4-D) digital model of the spatial volume of one or more arterial segments determined from the medical image data. By way of example, the coronary model may include a cardiovascular model of the patient, model of the patient's ascending aorta and coronary artery tree, among others, or any combination thereof.

In some embodiments, the coronary model may include one or more characteristics and/or information associated with one or more locations of one or more arterial segments determined invasively (e.g., via a scanning modality or medical device), non-invasively (computationally), or any combination thereof. In some embodiments, the one or more characteristics and/or information may include metrics or values associated with anatomical or geometrical information for each arterial segment, the one or more characteristics at least for each arterial segment, among others, or any combination thereof. The one or more characteristics may include one or more characteristics for each segment (also referred to as "one or more segment characteristics") such as one or more flow field characteristics for each segment, one or more hemodynamic characteristics for each segment (e.g. one or more hemodynamic force characteristics, one or more pressure characteristics, etc.), among others, or any combination thereof.

In some embodiments, the coronary model may optionally include location and/or information associated with one or more lesions/lesion sites. In some embodiments, the one or more characteristics may include one or more lesion characteristics, such as volume of plaque material, size, shape, one or more material properties, one or more mechanical properties, among others, or any combination thereof.

The coronary model, boundary conditions, and/or values of the one or more characteristics and/or information may have been generated, calculated, measured, and/or obtained using various invasive methods, non-invasive methods, or combination of methods, such as methods using physiology-derived features, physics-derived features, allometric scaling laws (e.g., Murray's law), data assimilation, machine-learning, among others, or combination of methods.

In some embodiments, the anatomical or geometrical information may include but is not limited to vessel size, radius, diameter, circumference, area, vessel thickness, vessel wall properties, among others, or any combination thereof.

In some embodiments, the flow field characteristics may include but is not limited to pressure field, velocity field, among others, or any combination thereof. In some embodiments, the one or more hemodynamic characteristics may include but is not limited to one or more pressure characteristics, one or more hemodynamic force characteristics, among others, or any combination thereof. The one or more pressure characteristics may include fractional flow reserve (FFR), instantaneous wave-free ratio (iFR), absolute flow reserve (aFR), relative flow reserve (RFR), diastolic pressure ratio (dPR), other pressure characteristic(s) (e.g., pressure across the segment, pressure difference across the segment, etc.), among others, or any combination thereof. In some embodiments, the one or more hemodynamic force characteristics may include wall shear stress (WSS), axial plaque stress (APS), etc.), among others, or any combination thereof.

In some embodiments, the coronary model may include boundaries associated with the geometrical representation, geometrical or anatomical information associated with each boundary, among others, or any combination thereof. For each segment, the boundaries may include inflow boundary, one or more outflow boundaries, vessel wall boundaries, among others, or any combination thereof.

In some embodiments, the coronary model may include boundary conditions associated with the geometrical representation, for example, used in the determination of the hemodynamic characteristics. The one or more boundary conditions may include inflow boundary conditions, one or more outflow boundary conditions, and one or more vessel wall boundary conditions.

In some embodiments, the step 210 may alternatively include one or more steps for constructing or generating a coronary model for the patient from at least medical image data of the patient acquired by a medical imaging system, determining the boundary conditions, determining boundaries, determining the one or more values of one or more characteristics and/or information, among others, or any combination thereof. By way of example, the method 200 may include one or more steps of a method 400 shown in FIG. 4. It will be understood that the one or more steps for constructing the coronary model, determining the boundary conditions, determining the boundaries, determining the one or more characteristics and/or information is not limited to the method 400 and may be performed using any available method. For example, the coronary model, boundary conditions, and/or values of one or more characteristics and/or information may be generated, calculated, measured, and/or obtained using available methods, such as methods using empirical laws, physiology-derived features, physics-derived features, allometric scaling laws (e.g., Murray's law), Navier-Stokes equations, data assimilation, machine learning, among others, or any combination thereof.

In some embodiments, the method 200 may include a step 220 of identifying one or more lesion sites disposed along one or more segments of the coronary model. In some embodiments, a lesion site may include a lesion, stenosis, and/or plaque. In some embodiments, each lesion site may include a region of the segment before and/or after the lesion, stenosis and/or plaque. In some embodiments, the one or more lesion sites may include one or more of a point, area, volume, cross-section, portion, and/or region within the one or more segments of the coronary model.

In some embodiments, if step 220 includes identifying one or more lesion sites, the one or more lesion sites may be identified using available methods. For example, each lesion site may be identified by splitting or segmentation of the segment using one or more hemodynamic characteristics for the corresponding segment, the anatomical or geometrical information, image-related features (e.g., intensity variations), among others, or any combination thereof. For example, a lesion site may be identified by a change in lumen diameter or radius. By way of example, the change may include a narrowing at one or more points of the segment. For example, the change may be determined by comparing the vessel diameter or radius at one or more points of the segment to other points of the segment and/or to a reference measurement of the lumen (e.g., a healthy lumen). The actual lumen measurement and/or reference measurement may be calculated, measured, and/or obtained using various invasive methods, non-invasive methods, or combination of methods, such as methods using machine learning, physiology-derived features, data assimilation, allometric scaling laws (e.g., Murray's law), among others, or any combination thereof.

In some embodiments, the step 220 may optionally include determining a stenosis index for each lesion site. In some embodiments, the stenosis index for a lesion site may indicate the functional severity associated with that lesion site. The stenosis index may be determined using the one or more information/characteristics associated with the segment. For example, in some embodiments, the stenosis index for each lesion site may be based on one or more pressure characteristics, such as fractional flow reserve (FFR), calculated for the corresponding segment.

In some embodiments, the size or length of a lesion site may be based on a fixed distance proximal or distal to a detected lesion. This distance may be predetermined or selected by a user on a user interface. For example, for a lesion, a lesion site may include a set distance (e.g., x millimeters) proximal or distal to the determined location of a lesion. In some embodiments, the fixed distance may be based on the severity of the lesion (e.g., stenosis index). For example, a more severe lesion may have a lesion site that could span a greater distance proximal and distal to the detected lesion.

In some embodiments, the stenosis index may be used to identify one or more lesion sites to be analyzed for a risk for a cardiovascular event, such as a risk of myocardial infarction, due to that lesion site. The stenosis index may be used to identify one or more lesion sites having a severity that can be considered functionally significant (i.e., that may require medical or revascularization and/or may cause ischemia).

In one example, the one or more lesion sites having a stenosis index considered to be functionally significant may correspond to the site(s) that are identified and analyzed for a risk of myocardial infarction. In some embodiments, the one or more lesion sites considered to be functionally significant may be determined using any available methods, using a statistical, threshold, machine-learning-based methods, among others, or any combination thereof.

For example, after determining the stenosis index for one or more sites, the step 220 may further include selecting one or more lesion sites having a stenosis index above or below a threshold. For example, if step 220 uses one or more pressure characteristics (e.g., an FFR value) as the stenosis index to identify one or lesion sites, the one or more lesion sites disposed along a segment having a value for the one or more pressure characteristics (e.g., an FFR value) below the threshold may be identified as the one or more lesion sites to be analyzed. The threshold may be based on a predefined value, value determined by machine learning, among others, or any combination thereof. By way of example, the threshold for FFR value may be one or more values within and including the range of 0.7-0.8. In this example, the one or more lesion sites having an FFR value below that threshold may have a stenosis index indicating that the lesion site may be functionally significant.

In some embodiments, the stenosis index may be determined using additional and/or alternative information/characteristic(s), available method(s) (e.g., machine learning), or any combination thereof. For example, the stenosis index may also be determined using one or more lesion characteristics.

In some embodiments, the one or more lesion sites, the information associated with each site (e.g., stenosis index and/or one or more lesion characteristics, etc.), among others, or any combination thereof may be received or retrieved with the received coronary model (in step 210). In some embodiments, the step 220 may be a separate step of retrieving or receiving the one or more lesion sites associated with the coronary model In some embodiments, the method 200 may include a step 230 of segmenting each lesion site into one or more sections. In some embodiments, the segmenting may be based on a location of that lesion site relative to the arterial segment, minimal lumen area, among others, or any combination thereof. The one or more lesion sites may include any number of sections. For example, for each lesion site, the one or more sections may include but are not limited to: one section, three sections, or five sections. The more than one section may be of same size or length, different size or length (e.g., bigger or smaller), or any combination thereof.

For example, using the location relative to the arterial segment, the one or more sections may include: proximal section of the lesion, intermediate section of the lesion, and distal section of the lesion. In this example, the proximal section may be closest to the inflow boundary (upstream); the middle section may be between the proximal section and the distal section; and the distal section may closest to the outflow boundary (downstream). By way of example, each of these sections may be of the same length or size relative to the corresponding arterial segment.

In some embodiments, the one or more sections may also include an upstream section (a region next to the proximal section) and/or a downstream section (a region next to the distal section). In some embodiments, the upstream and/or downstream sections may be of same size or length of the other sections (e.g., proximal, intermediate, or distal); a different size, or any combination thereof. For example, the size or length of the upstream and/or downstream section may be determined based on the size of the proximal, intermediate and/or distal sections; based on a fixed distance (e.g., defined by the user, the stenosis index, among others, or any combination thereof); based on other factors; or any combination thereof. It will be understood that each lesion site may include more sections, less sections, and/or different alternative sections.

In some embodiments, the method 200 may further include a step 240 of determining one or more characteristics for one or more sections of each lesion site (can also be referred to as "one or more lesion site characteristics"). This way, the characteristic(s) can be determined relative to a location within the lesion site.

In some embodiments, the characteristic(s) may be determined for at least one section of each lesion site, such as the proximal section. In some embodiments, the characteristic(s) may be determined for more sections of the lesion site. For example, using the one or more characteristics (e.g., flow field characteristic(s), hemodynamic characteristic(s), etc.) determined for the segment, the one or more characteristics across a section of a lesion site disposed in that segment may be determined. For example, using the one or more hemodynamic characteristics for a segment, the one or more hemodynamic characteristics for a section disposed in that segment may correspond to the average or median hemodynamic characteristic for that section.

In some embodiments, the one or more characteristics determined for the one or more sections of each lesion site may include but is not limited to the one or more hemodynamic characteristics, the one or more lesion characteristics, the one or more flow field characteristics, among others, or any combination thereof. For example, the one or more hemodynamic characteristics may include the one or more pressure characteristics, the one or more hemodynamic force characteristics, among others, or any combination thereof. As mentioned previously, the one or more pressure characteristics may include but is not limited to fractional flow reserve (FFR), instantaneous wave-free ratio (iFR), absolute flow reserve (aFR), relative flow reserve (RFR), diastolic pressure ratio (dPR), other pressure characteristic(s) (e.g., pressure across the segment, pressure difference across the segment, etc.), among others, or any combination thereof and the one or more hemodynamic force characteristics may include but is not limited to wall shear stress (WSS), axial plaque stress (APS), among others, or any combination thereof.

In some embodiments, the step 240 may include determining at least one or more hemodynamic force characteristics for the one or more sections of each lesion site. In some embodiments, the one or more hemodynamic force characteristics may include at least determining the WSS for the one or more sections of each lesion site. In some embodiments, the WSS for each section of a lesion site may be determined by calculating the average (mean), median, among others, or any combination thereof, of circumferential wall shear stress across the surface of that section. In some embodiments, the WSS may be determined relative to a medial axis of the lumen, for example, along or parallel to the medial axis, perpendicular to the medial axis, among others, or any combination thereof.

In some embodiments, the WSS may be determined using the velocity field. In some embodiments, the APS may be determined using both the pressure and velocity fields.

Next, the method 200 may include a step 250 of generating one or more risk indices associated with each lesion site using at least one or more characteristics for one or more sections of the lesion site. The one or more risk indices for a lesion site may be a value and/or metric indicative of a probability of a myocardial infarction (e.g., myocardial infarction event) due to or from the lesion site.

By way of example, the one or more risk indices for a lesion site may relate to a level of risk of a myocardial infarction (e.g., myocardial infarction) due to that lesion site. For example, the level of risk may be high or low. The risk indices are not limited to indicating a high risk and a low risk of a myocardial infarction. The risk indices may indicate additional or alternative levels of risk (e.g., moderate or intermediate level of risk), include value(s) representing the probability of a myocardial infarction, among others, or any combination thereof.

In some embodiments, the step 250 may include comparing the values of the one or more characteristics to one or more thresholds to determine the one or more risk indices. The threshold values are not limited to the value and characteristic discussed below and may be different. The threshold values may be predefined, dependent on other factors, associated with alternative or additional characteristic(s), determined by various available methods (e.g., methods using statistical analysis, machine learning, among others, or any combination thereof), among others, or any combination thereof.

In some embodiments, the one or more risk indices for each lesion site may be determined using at least the values of one or more hemodynamic force characteristics for one or more sections of each lesion site. In some embodiments, the one or more risk indices for each lesion site may be determined using at least the WSS for the proximal section for each lesion site.

For example, if the one or more risk indices for the lesion site is based on at least the WSS value, the step 250 may include comparing the WSS value determined for one or more sections to a threshold value, such as 4.71 Pa, to determine a risk index for that lesion site. By way of example, if the WSS for the one or more sections of a lesion site is higher than the threshold, then step 250 may determine that the risk index for that lesion site indicates a high risk (e.g., a high probability of the patient experiencing a myocardial infarction). In this example, if the average WSS value for each of the sections of the lesion site are equal to and/or lower than the threshold, then step 250 may determine that the risk index for that lesion site indicates a low risk. In some embodiments, the WSS value may be for only the proximal section of the lesion site. In some embodiments, the WSS value for other sections of the lesion site may be used in the determination of the one or more risk indices.

In some embodiments, the one or more risk indices for one or more sections of the lesion site may also be determining using at least another characteristic and/or information, such as at least another characteristic of the one or more other hemodynamic characteristics, stenosis index, one or more lesion characteristics, among others, or any combination thereof.

By way of example, one or more risk indices may also be determined using one or more pressure characteristics, such as at least FFR value (or stenosis index), for one or more sections of the lesion site. For example, the step 250 may determine one or more risk indices by comparing both the FFR and WSS values for one or more sections to one or more threshold values. For example, for a lesion site having an FFR value below the threshold and an WSS value equal to and/or below the threshold, the step 250 may determine a risk index for that lesion that indicates a low or intermediate risk. In this example, for a lesion site having an FFR value below the threshold and an WSS value above the threshold, the step 250 may determine a risk index for that lesion indicates a high or intermediate risk. For a lesion site having an FFR value above or equal to the threshold, the step 250 may determine a risk index for that lesion site indicates a low risk. In some embodiments, the lesion sites that have a stenosis index that does not indicate to be functionally significant may be determined to have a risk index that is low.

In some embodiments, the determination between levels of risk may be based on other information, such as other hemodynamic characteristic(s), one or more lesion characteristics, among others, or any combination thereof.

In some embodiments, the one or more risk indices may be determined using other available methods, such as statistical methods, machine-learning-based methods, among others, or any combination thereof.

In some embodiments, the step 250 may include determining a treatment option (e.g., a suggested lesion to treat, recommended method for treatment, etc.) using at least the one or more risk indices. In some embodiments, a treatment option may optionally be determined using other information/characteristic(s), among others, or any combination thereof. The treatment options may include but are not limited to lifestyle changes, medical therapy, revascularization (such as PCI, CABG, among others, or any combination thereof). For example, if the risk index for a lesion site indicates a high risk, the treatment recommendation can include revascularization and medical therapy. If the risk index for a lesion site indicates a low risk, the treatment recommendation may be medical therapy only.

In some embodiments, the method 200 may include a step of 260 of outputting the one or more risk indices for each lesion site, treatment option(s) for each site, among others, or any combination thereof. The outputting may include but is not limited to displaying the one or more risk indices (with or without the recommended treatment options) for the one or more lesion sites, outputting the one or more risk indices for the one or more lesion sites to an electronic storage medium, among others, or any combination thereof.

In some embodiments, the step 260 may include generating a visualization of the one or more lesion sites for display, storage, among others, or any combination thereof.

In some embodiments, the visualization may include a representation of the vasculature, such as the generated coronary model, that includes the one or more lesion sites. By way of example, the one or more lesion sites, the location of the one or more sections of the lesion site, recommended treatment option(s), or any combination thereof may be identified on the coronary model, for example, by one or more visual indicators, such as a marker (e.g., pin, among others, or any combination thereof), color, among others, or any combination thereof.

In some embodiments, the visualization may include the values of the hemodynamic characteristics, indices, among others, or any combination thereof, associated with the one or more sections of the lesion site(s). In some embodiments, the values associated with the lesion site(s) may be provided in a table, graph, histogram, etc.

In some embodiments, one or more of the hemodynamic characteristics, the one or more risk indices, treatment option(s), among others, or any combination thereof, may be associated with corresponding lesion site, for example, by being overlaid on a representation of the coronary model, by being visualized by one or more visual indicators, among others, or any combination thereof.

In some embodiments, the visualization may include colors, shades, patterns, or other visual indicators to represent different values or range of values (e.g., above or below a threshold) of one or more of the characteristics (e.g., hemodynamic characteristic(s)), the one or more risk indices, one or more treatment options, among others, or any combination thereof. In some embodiments, the colors or other indicators may additionally or alternatively represent sections of the one or more lesion sites.

Figure 3A:
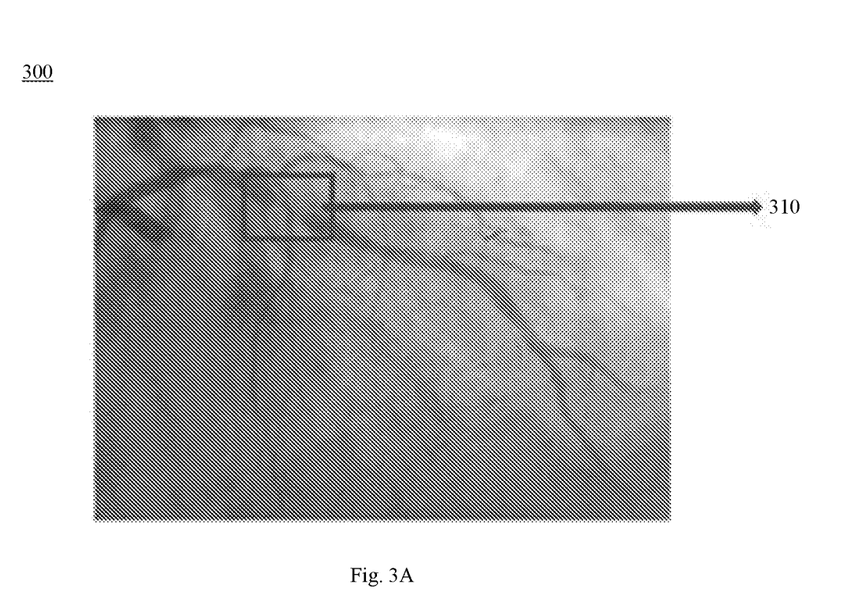
FIG. 3A shows an example of angiographic biplane image of coronary lumens of a patient.
Figure 3B:
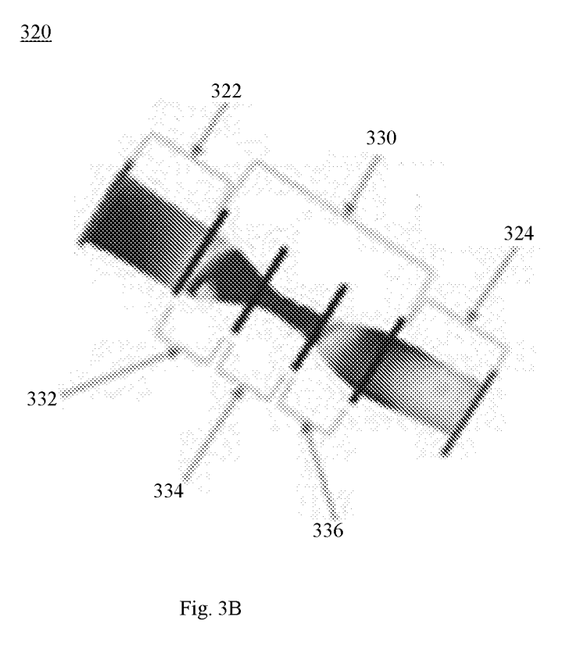
FIG. 3B shows an example of a coronary model of a lesion site for the vessel lumen identified by a box in FIG. 3A with color variations corresponding to the calculated hemodynamic force characteristic(s)
Figure 3C:
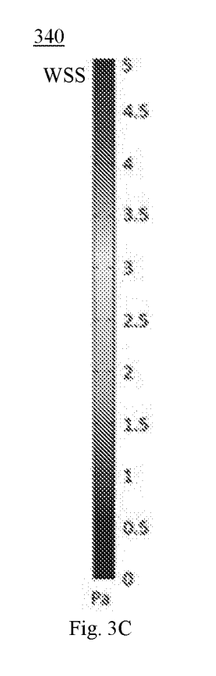
FIG. 3C shows a scale showing the color variations associated with the value of the hemodynamic force characteristic(s)

FIGS. 3 A-C show an example of a risk index for a lesion site along a segment that has been determined using angiographic images of a patient according to embodiments. FIG. 3A shows an example of angiographic image projections 300; FIG. 3B shows an example of lesion site 320 identified on a constructed 3-dimensional coronary model for a coronary vessel lumen identified in the box 310 in FIG. 3A with colors (e.g., variations in gray scale) representing different values of WSS/risk index; and FIG. 3C shows a scale 340 showing the WSS/risk index value associated with the color variations.

To generate the 3-dimension coronary model shown in FIG. 3B, a 3-dimensional geometric representation of the vessel lumen (e.g., segment) can be generated using the angiographic images, computational fluid dynamics can be performed with the patient-specific boundary conditions. The lesion site 320 can be identified and segmented into one or more sections using any of the methods discussed. After which, the section-specific wall shear stress values can be determined.

As shown in FIG. 3B, the segment of the coronary lumen includes a lesion site 320. The lesion site 320 includes a lesion 330 that has been segmented into three sections: proximal 332, middle 334 and distal 336. In this example, the lesion site 320 may also include the area surrounding the lesion 330. As shown in FIG. 3B, the lesion site 320 may also be segmented into an upstream section 322 and a downstream section 324 relative to the lesion 330. In this example, the (average) wall shear stress (WSS) has been calculated for each section of the lesion 320. The sections of the lesion are colored based on the wall shear stress, according to the scale shown in FIG. 3C. corresponding to the lesion disposed adjacent to the generated model.

Using a threshold value of 4.71 Pa for determination of risk indices using WSS, the method 200 may determine that the risk index for the lesion site 320 may indicate a high risk of myocardial infarction. As shown in this example, the WSS for at least the proximal section 332 is above 4.71 Pa.

In some embodiments, the visualization may be an interactive user interface to be presented to the user on a display device. The interactive user interface may allow the user to view values associated with one or more hemodynamic characteristics for one or more locations along the coronary model. In some embodiments, the interactive user interface may allow the user to select different treatment options.

In some embodiments, the step 260 may include enabling the assessment of one or more treatment options based on at least the one or more risk indices. In some embodiments, the interactive user interface may allow the user to select the location for a proposed treatment on the vasculature, select the parameters for treatment, and/or simulate the results of the treatment. In some embodiments, the assessment of various treatment options may also include, for example, an optimization of a treatment based on the simulation of results for various treatment options.

By way of example, the user may modify the coronary model to assess one or more treatments, e.g., medical, percutaneous or coronary interventions (e.g., revascularization (e.g., placing a coronary stent at a lesion site (e.g., virtual stenting to thereby remove one or more stenosis)), simulate the effect of progression or regression of the lesion (or other disease), in one or more of the coronary arterial segments represented in the geometrical representation. Then, a computational analysis may be performed to generate an updated coronary model and one or more risk indices, for example, to determine whether there is a reduction in the one or more risk indices if the treatment option(s) is adopted. The updated coronary model and/or one or more risk indices may be displayed to the user (e.g., clinician) on the user interface.

In some embodiments, the step may include outputting the determined treatment option to display or an electronic storage medium.

Figure 4:
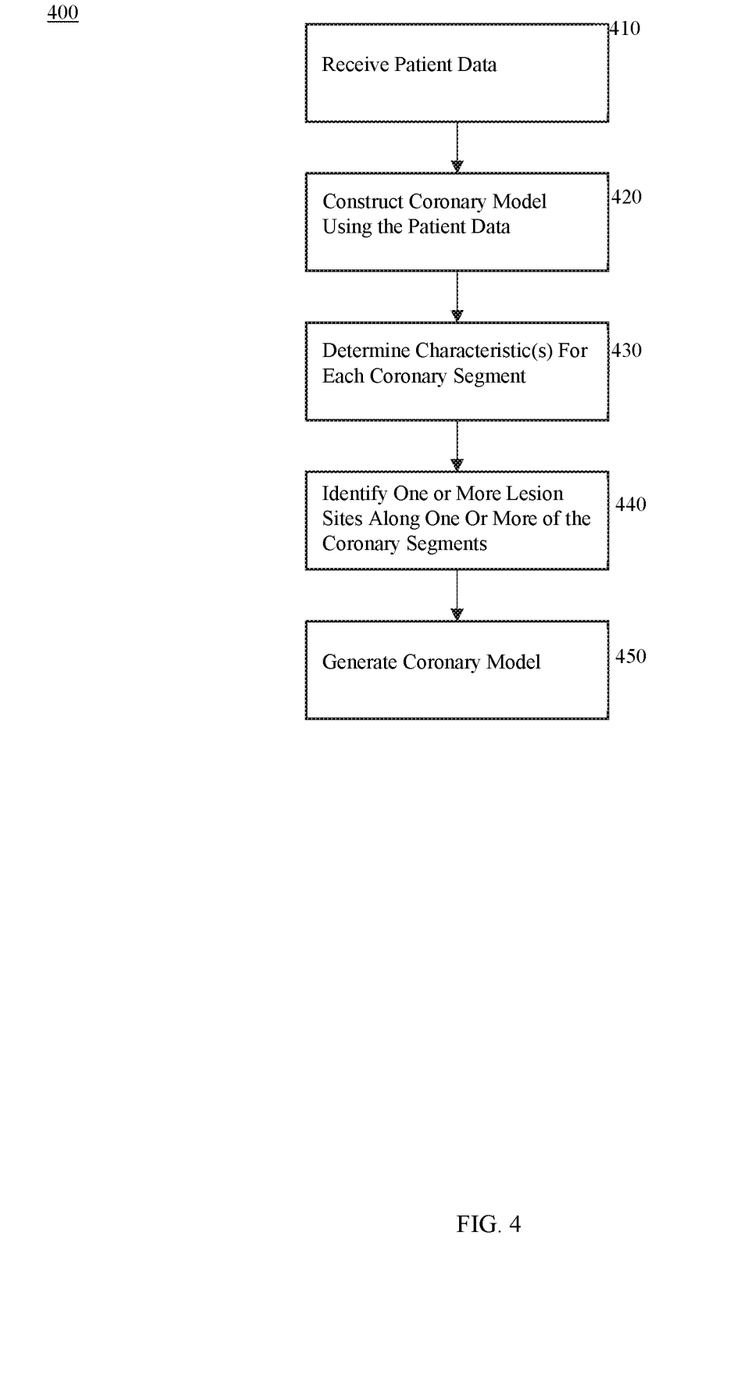
FIG. 4 shows an example of a method of determining a coronary model according to some embodiments.

FIG. 4 shows an example of a method for generating a coronary model according to some embodiments. In some embodiments, the method 200 may include generating the coronary model based on the received medical image data using the method 400, other available methods, or any combination thereof.

In some embodiments, the method 400 may include a step 410 of receiving medical image data (also referred to as 'image data" of a patient). In some embodiments, the patient data may include medical image data of a patient acquired by a medical imaging system, such as the medical imaging system 110. The medical image data from one or more medical image acquisition devices may include but are not limited to CT, Dyna CT, magnetic resonance (MR), angiography, ultrasound, OCT, single photon emission computed tomography (SPECT), among others, or any combination thereof. The image data may include one or more regions of surrounding blood vessels, including the arteries, of a patient.

By way of example, the medical image data may be digitized image data obtained from a plurality of cardiac CT scans of a patient using a clinical CT system. In some embodiments, the image data may include one or more image slices of a region of interest which may include the arteries of interest and surrounding blood vessel. In addition to CT images, the image data may be from other sources, such as angiography (e.g., biplane angiography), intravascular ultrasound (IVUS), optical coherence tomography (OCT), magnetic resonance imaging (MRI), among others, or combination thereof.

In some embodiments, the image data of the patient may be presented to the user to select the one or more arterial segments for which the myocardial risk should be analyzed. In the alternative, the system may automatically determine the one or more arterial segments for which the myocardial risk should be analyzed.

In some embodiments, the patient data may include demographic data, physiological data (e.g., blood pressure, baseline heart rate, height, weight, hematocrit, stroke volume, etc.), blood markers data, other types of data, among others, or any combination thereof. For example, the blood pressure may be the blood pressure in the patient's brachial artery (e.g., measured using a pressure cuff), such as the maximum (systolic) and minimum (diastolic) pressures.

Next, in some embodiments, the method 400 may include a step 420 of constructing a coronary model using the patient data. By way of example, the coronary model may include a cardiovascular model of the patient or model of the patient's ascending aorta and coronary artery tree.

The step 420 may include generating a patient specific geometrical representation for one or more arterial segments using the image data. In some embodiments, the geometrical representation may be a multi-dimensional (e.g., 3-D or 4-D) digital model of the spatial volume of one or more arterial segments.

The step 420 may also include determining boundaries for each arterial segment and geometrical data associated with each boundary for each segment. For each segment, the boundaries may include inflow boundary, one or more outflow boundaries, vessel wall boundaries, among others, or any combination thereof. For example, in this step, the geometrical data may include the radii for the inflow boundary and for one or more outflow boundaries.

The step 420 may include determining one or more boundary conditions for each segment of the geometrical representation. The one or more boundary conditions may include inflow boundary conditions, one or more outflow boundary conditions, and one or more vessel wall boundary conditions.

The step 420 may include determining geometrical information for each boundary of each segment using the generated geometric representation. In some embodiments, the geometrical information may include but is not limited to radius, diameter, circumference, area, among others, or any combination thereof.

In some embodiments, the coronary model, including the boundary conditions, the boundaries, and/or the geometrical information, etc., may be generated, calculated, measured, and/or obtained using any available methods including various invasive methods, non-invasive methods, or combination of methods, such as methods using empirical laws, physiology-derived features, physics-derived features, allometric scaling laws (e.g., Murray's law), Navier-Stokes equations, data assimilation, machine learning, among others, or any combination thereof.

In some embodiments, the method 400 may include a step 430 of determining one or more characteristics for each segment (can also be referred to as "segment characteristics") using available methods.

In some embodiments, the one or more segment characteristics may include one or more flow field characteristics, one or more hemodynamic characteristics, among others, or any combination thereof.

In some embodiments, the one or more flow field characteristics may include but is not limited to pressure field, velocity field, among others, or any combination thereof. In some embodiments, the one or more hemodynamic characteristics may include but is not limited to one or more pressure characteristics, one or more hemodynamic force characteristics, among others, or any combination thereof. In some embodiments, the one or more pressure characteristics may include one or more fractional flow reserve (FFR), instantaneous wave-free ratio (iFR), absolute flow reserve (aFR), relative flow reserve (RFR), diastolic pressure ratio (dPR), other pressure characteristic(s) (e.g., pressure across the segment, pressure difference across the segment, etc.), among others, or any combination thereof. In some embodiments, the one or more hemodynamic force characteristics may include wall shear stress (WSS), axial plaque stress (APS), among others, or any combination thereof.

In some embodiments, the one or more characteristics associated with the coronary model may be determined using any available methods including various invasive methods, non-invasive methods, or combination of methods, such as methods using empirical laws, physiology-derived features, physics-derived features, allometric scaling laws (e.g., Murray's law), Navier-Stokes equations, data assimilation, machine learning, among others, or any combination thereof.

For example, the pressure drop values across one or more lesion sites can be computed non-invasively, for example using computational fluid dynamics (CFD) or other computational approaches such as machine-learning based approaches, or measured invasively, and these values can be used to compute the one or more pressure characteristics, such as fractional flow reserve (FFR).

By way of example, the hemodynamic force characteristics on the lumen wall may be computed, using available methods, to obtain a continuous representation of the hemodynamic characteristics on the lumen wall (that is by interpolation). For example, methods using the incompressible Navier-Stokes equations as a model for blood flow, including machine-learning methods, may be used. By way of another example, the hemodynamic force characteristics can be extracted from the computed pressure fields and the computed velocity fields.

In some embodiments, the method 400 may optionally include a step 440 of determining one or more lesion sites, for example, using the method described in step 220 as well as any available methods. In some embodiments, the step 440 may be omitted and performed in the method 200.

In some embodiments, the method 400 may include a step 450 of generating the coronary model, for example, based on at least steps 410-430, for display, storage (e.g., in the patient record storage 120), transmission to the risk index determination device 130, among others, or any combination thereof.

One or more of the devices and/or systems of the system 100 may be and/or include a computer system and/or device. FIG. 5 is a block diagram showing an example of a computer system 500. The modules of the computer system 500 may be included in at least some of the systems and/or modules, as well as other devices and/or systems of the system 100.

The system for carrying out the embodiments of the methods disclosed herein is not limited to the systems shown in FIGS. 1 and 5. Other systems may also be used. It is also to be understood that the system 500 may omit any of the modules illustrated and/or may include additional modules not shown.

The system 500 shown in FIG. 5 may include any number of modules that communicate with each other through electrical or data connections (not shown). In some embodiments, the modules may be connected via any network (e.g., wired network, wireless network, or any combination thereof).

The system 500 may be a computing system, such as a workstation, computer, or the like. The system 500 may include one or more processors 512. The processor(s) 512 (also referred to as central processing units, or CPUs) may be any known central processing unit, a processor, or a microprocessor. The CPU 512 may be coupled directly or indirectly to one or more computer—readable storage media (e.g., memory) 514. The memory 514 may include random access memory (RAM), read only memory (ROM), disk drive, tape drive, etc., or any combination thereof. The memory 514 may be configured to store programs and data, including data structures. In some embodiments, the memory 514 may also include a frame buffer for storing data arrays.

In some embodiments, another computer system may assume the data analysis or other functions of the CPU 512. In response to commands received from an input device, the programs or data stored in the memory 514 may be archived in long term storage or may be further processed by the processor and presented on a display.

In some embodiments, the system 500 may include a communication interface 516 configured to conduct receiving and transmitting of data between other modules on the system and/or network. The communication interface 516 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 510 may include an input/output interface 518 configured for receiving information from one or more input devices 520 (e.g., a keyboard, a mouse, and the like) and/or conveying information to one or more output devices 520 (e.g., a printer, a CD writer, a DVD writer, portable flash memory, etc.). In some embodiments, the one or more input devices 520 may be configured to control, for example, the generation of the management plan and/or prompt, the display of the management plan and/or prompt on a display, the printing of the management plan and/or prompt by a printer interface, the transmission of a management plan and/or prompt, among other things.

In some embodiments, the disclosed methods (e.g., FIGS. 2 and 4) may be implemented using software applications that are stored in a memory and executed by a processor (e.g., CPU) provided on the system 100. In some embodiments, the disclosed methods may be implemented using software applications that are stored in memories and executed by CPUs distributed across the system.

As such, any of the systems and/or modules of the system 100 may be a general purpose computer system, such as system 500, that becomes a specific purpose computer system when executing the routines and methods of the disclosure. The systems and/or modules of the system 100 may also include an operating system and micro instruction code. The various processes and functions described herein may either be part of the micro instruction code or part of the application program or routine (or combination thereof) that is executed via the operating system.

If written in a programming language conforming to a recognized standard, sequences of instructions designed to implement the methods may be compiled for execution on a variety of hardware systems and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 5. It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A computer-implemented method of determining a risk of myocardial infarction associated with a coronary lesion of a patient, the method comprising:
   receiving a patient-specific coronary model of at least a portion of a vasculature of the patient, the patient-specific coronary model including a geometrical representation of the one or more arterial segments;
   the patient-specific coronary model including one or more characteristics associated with each arterial segment;
   segmenting each lesion site disposed along at least one arterial segment of the one or more arterial segments into three or more sections;
   each lesion site including a lesion;
   the segmenting of each lesion site into the three or more sections is based on a location of the lesion of each lesion site relative to corresponding arterial segment;
   the three or more sections for each lesion site includes a proximal section, the proximal section being adjacent to inflow boundary of the corresponding arterial segment;
   determining one or more characteristics for at least of the proximal section of each lesion site using at least the one or more characteristics associated with the at least one arterial segment;
   the one or more characteristics for at least the proximal section including one or more hemodynamic force characteristics, the one or more hemodynamic force characteristics for the at least one section including at least wall shear stress (WSS); and
   determining one or more risk indices for each lesion site using at least the one or more hemodynamic force characteristics for at least the proximal section of each lesion site, the one or more risk indices for each lesion site indicating a risk of a myocardial infarction event from each lesion site.

2. The method according to claim 1, wherein the determining the one or more hemodynamic force characteristics for at least the proximal section of each lesion site includes averaging the one or more hemodynamic force characteristics along at least the proximal section of the lesion site using the one or more hemodynamic force characteristics for the at least one arterial segment.

3. The method according to claim 1, further comprising:
   identifying one or more lesion sites disposed along the at least one arterial segment of the one or more arterial segments, each lesion site including the lesion;
   wherein the one or more characteristics associated with each arterial segment and each lesion site includes one or more hemodynamic characteristics, the one or more hemodynamic characteristics including one or more pressure characteristics, the one or more pressure characteristics including fractional flow reserve (FFR); and
   wherein the one or more lesion sites is identified and/or the one or more risk indices is determined using at least the one or more pressure characteristics for at least the proximal section of each lesion site and/or for each arterial segment.

4. The method according to claim 1, wherein:
   the determining the one or more risk indices includes comparing at least the one or more hemodynamic force characteristics for at least the proximal section of each lesion site to one or more thresholds.

5. The method according to claim 1, further comprising:
   generating a visualization of at least one lesion site; and
   outputting the visualization.

6. The method according to claim 5, wherein the visualization includes (i) the one or more risk indices associated with the at least one lesion site and/or (ii) the one or more characteristics associated with the at least one lesion site and/or the one or more arterial segments.

7. The method according to claim 1, further comprising:
   enabling an assessment of treatment options for each lesion site, based on the one or more risk indices and/or the one or more characteristics associated with at least the proximal section of each lesion site.

8. The method according to claim 1, further comprising:
   receiving patient data of the patient, the patient data including medical image data of the patient acquired by a medical image acquisition device, the medical image data including the one or more arterial segments and surrounding area; and
   generating the patient-specific coronary model using the patient data, the coronary model including the geometrical representation of the one or more arterial segments from the medical image data, boundaries for each arterial segment, boundary conditions for each arterial segment, geometrical information for each boundary, and geometrical information;
   wherein the generating includes generating the one or more characteristics for each arterial segment; and
   wherein the one or more characteristics for each arterial segment includes one or more flow field characteristics and one or more hemodynamic characteristics.

9. A system for determining a risk of myocardial infarction associated with a coronary lesion of a patient, the system comprising:
   at least one processor; and
   a memory, wherein the processor is configured to cause:
      receiving a patient-specific coronary model of at least a portion of a vasculature of the patient, the patient-specific coronary model including a geometrical representation of the one or more arterial segments;
      the patient-specific coronary model including one or more characteristics associated with each arterial segment;

segmenting each lesion site disposed along at least one arterial segment of the one or more arterial segments into three or more sections;

each lesion site including a lesion;

the segmenting of each lesion site into the three or more sections is based on a location of the lesion of each lesion site relative to corresponding arterial segment;

the three or more sections for each lesion site includes a proximal section, the proximal section being adjacent to inflow boundary of the corresponding arterial segment;

determining one or more characteristics for at least the proximal section each lesion site using at least the one or more characteristics associated with the at least one arterial segment;

the one or more characteristics for at least the proximal section including one or more hemodynamic force characteristics, the one or more hemodynamic force characteristics for the at least one section including at least wall shear stress (WSS); and determining one or more risk indices for each lesion site using at least the one or more hemodynamic force characteristics for at least the proximal section of each lesion site, the one or more risk indices for each lesion site indicating a risk of a myocardial infarction event from each lesion site.

10. The system according to claim 9, wherein the determining the one or more hemodynamic force characteristics for at least the proximal section of each lesion site includes averaging the one or more hemodynamic force characteristics along at least the proximal section of the lesion site using the one or more hemodynamic force characteristics for the at least one arterial segment.

11. The system according to claim 9, wherein the processor is further configured to cause:

identifying one or more lesion sites disposed along the at least one arterial segment of the one or more arterial segments, each lesion site including the lesion;

wherein the one or more characteristics associated with each arterial segment and each lesion site includes one or more hemodynamic characteristics, the one or more hemodynamic characteristics including one or more pressure characteristics, the one or more pressure characteristics including fractional flow reserve (FFR); and wherein the one or more lesion sites is identified and/or the one or more risk indices is determined using at least the one or more pressure characteristics for at least the proximal section of each lesion site and/or for each arterial segment.

12. The system according to claim 9, wherein:

the determining the one or more risk indices includes comparing at least the one or more hemodynamic force characteristics for at least the proximal section of each lesion site to one or more thresholds.

13. The system according to claim 9, wherein the processor is further configured to cause:

generating a visualization of at least one lesion site; and outputting the visualization.

14. The system according to claim 13, wherein the visualization includes (i) the one or more risk indices associated with the at least one lesion site and/or (ii) the one or more characteristics associated with the at least one lesion site and/or the one or more arterial segments.

15. The system according to claim 9, wherein the processor is further configured to cause:

enabling an assessment of treatment options for each lesion site, based on the one or more risk indices and/or the one or more characteristics associated with at least the proximal section of each lesion site.

16. The system according to claim 9, wherein the processor is further configured to cause:

receiving patient data of the patient, the patient data including medical image data of the patient acquired by a medical image acquisition device, the medical image data including the one or more arterial segments and surrounding area; and generating the patient-specific coronary model using the patient data, the coronary model including the geometrical representation of the one or more arterial segments from the medical image data, boundaries for each arterial segment, boundary conditions for each arterial segment, geometrical information for each boundary, and geometrical information;

wherein the generating includes generating the one or more characteristics for each arterial segment; and wherein the one or more characteristics for each arterial segment includes one or more flow field characteristics and one or more hemodynamic characteristics.

* * * * *